(12) United States Patent
Slepian

(10) Patent No.: US 10,945,669 B2
(45) Date of Patent: Mar. 16, 2021

(54) FLOWABLE ELECTRONICS

(71) Applicant: The Arizona Board of Regents on Behalf of the University of Arizona, Tucson, AZ (US)

(72) Inventor: Marvin J. Slepian, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 536 days.

(21) Appl. No.: 15/517,897

(22) PCT Filed: Oct. 8, 2015

(86) PCT No.: PCT/US2015/054695
§ 371 (c)(1),
(2) Date: Apr. 7, 2017

(87) PCT Pub. No.: WO2016/057796
PCT Pub. Date: Apr. 14, 2016

(65) Prior Publication Data
US 2017/0303855 A1 Oct. 26, 2017

Related U.S. Application Data

(60) Provisional application No. 62/061,599, filed on Oct. 8, 2014.

(51) Int. Cl.
*A61B 5/00* (2006.01)
*A61N 1/36* (2006.01)
*A61B 5/04* (2006.01)

(52) U.S. Cl.
CPC .......... *A61B 5/6847* (2013.01); *A61B 5/0024* (2013.01); *A61B 5/6861* (2013.01);
(Continued)

(58) Field of Classification Search
CPC .......... A61B 2562/12; A61B 2562/164; A61B 2562/168; A61B 5/6847; A61B 5/6861
See application file for complete search history.

(56) References Cited

U.S. PATENT DOCUMENTS

| 2,675,619 A | 4/1954 | Cone |
| 2,677,700 A | 5/1954 | Jackson |
(Continued)

FOREIGN PATENT DOCUMENTS

EP     1847217     10/2007

OTHER PUBLICATIONS

Albertsson, et al., "The mechanism of biodegradation of polyethylene", Polymer Degradation and Stability, 18:73-87 (1987).
(Continued)

*Primary Examiner* — William H Matthews
(74) *Attorney, Agent, or Firm* — Pabst Patent Group LLP

(57) ABSTRACT

Electronic devices and systems that overcome the limitation of stiffness and rigidity generally associated with electronics and allow for delivery via minimally invasive or percutaneous access and delivery systems are described herein. The devices and systems are able to change in size, such as from a larger electronic construct to a smaller flowable configuration. The devices and systems are configured to open or reconfigure to return to the original size and spatial dimensions at the site. In another embodiment, the devices and systems begin as a plurality of discrete electrical elements in a flowable state, and change to a non-fluent state thereby forming an electrical construct. The electrical elements are able to communicate by direct contact with each other or near field inter-device communication means. This allows the electronic device or system to be applied, adhere and conform to the underlying surface.

20 Claims, 3 Drawing Sheets

(52) U.S. Cl.
CPC ........... *A61B 5/04* (2013.01); *A61B 2562/028* (2013.01); *A61B 2562/12* (2013.01); *A61B 2562/164* (2013.01); *A61B 2562/224* (2013.01); *A61N 1/36125* (2013.01)

(56) References Cited

U.S. PATENT DOCUMENTS

| | | |
|---|---|---|
| 2,979,578 A | 4/1961 | Cuttis |
| 3,036,118 A | 5/1962 | Jackson |
| 3,535,307 A | 10/1970 | Moss |
| 3,829,506 A | 8/1974 | Schmolka |
| 3,868,956 A | 3/1975 | Alfidi |
| 4,655,771 A | 4/1987 | Wallsten |
| 4,938,763 A | 7/1990 | Dunn |
| 5,213,580 A | 5/1993 | Slepian |
| 5,328,471 A | 7/1994 | Slepian |
| 5,545,291 A | 8/1996 | Smith |
| 5,575,815 A | 11/1996 | Slepian |
| 5,634,946 A | 6/1997 | Slepian |
| 5,674,287 A | 10/1997 | Slepian |
| 5,749,922 A | 5/1998 | Slepian |
| 5,807,258 A | 9/1998 | Cimochowski |
| 5,843,156 A | 12/1998 | Slepian |
| 5,863,024 A | 1/1999 | Blind |
| 5,947,977 A | 9/1999 | Slepian |
| 6,287,320 B1 | 9/2001 | Slepian |
| 6,290,729 B1 | 9/2001 | Slepian |
| 6,443,941 B1 | 9/2002 | Slepian |
| 6,699,272 B2 | 3/2004 | Slepian |
| 6,890,300 B2 | 5/2005 | Lloyd |
| 8,336,387 B2 | 12/2012 | Tai |
| 8,552,299 B2 | 10/2013 | Rogers |
| 2007/0161851 A1 | 7/2007 | Takizawa |
| 2009/0230174 A1 | 9/2009 | Kim |
| 2011/0237921 A1 | 9/2011 | Askin |
| 2013/0041235 A1 | 2/2013 | Rogers |
| 2014/0170457 A1 | 6/2014 | Wegner |

OTHER PUBLICATIONS

Ashton, et al, "Polymeric endoaortic paving: Mechanical, thermoforming, and degradation properties of polycaprolactone/polyurethane blends for cardiovascular applications," Acta Biomaterialia, 7(1), 287-94, (2011).
Avichat, et al, "Recent Investigations of Plant Based Natural Gums, Mucilages and Resins in Novel Drug Delivery Systems", Ind. J. Pharm. Edu. Res., 24(a):86-99 (2010).
Dagdeviren, et al., "Conformal piezoelectric energy harvesting and storage from motions of the heart, lung, and diaphragm," PNAS, 111(5): 1927-32 (2014).
Herrmann, et al., "Electric-Field Triggered Controlled Release of Bioactive Volatiles from Imine-Based Liquid Crystalline Phases", Chemistry, 15:117-24 (2009).
Ricker, et al, "Corrosion of Metals",Evaluation of Alternative In-Flight Fire Suppressants for Full-Scale Testing in Simulated Aircraft Engine Nacelles and Dry Bays. Section 7:669-728, edited by Grosshandler, et al. NIST (1994).
Rogers, et al., "Materials and mechanics for stretchable electronics" Science 327 (5973), 1603-7 (2010).
Slepian, et al., "Polymeric endoluminal paving. A family of evolving methods for extending endoluminal therapeutics beyond stenting", Cardiology Clinics, 12(4):715-37 (1994).
International Search Report in corresponding PCT application PCT/US2015/054695 dated Dec. 28, 2015.
Harada, et al., "A reconfigurable modular robotic endoluminal surgical system: vision and preliminary results", Robotica, 28(02):171-183 (2009).
Zambonelli, et al., "Spray computers: Explorations in self-organization", Pervasive and Mobile Computing, 1(1):1029 (2005).

FLOWABLE ELECTRONICS

CROSS-REFERENCE TO RELATED APPLICATION

This application is a 371 application of International Application No. PCT/US2015/054695, filed Oct. 8, 2015, which claims priority to and benefit of U.S. provisional application No. 62/061,599, entitled "Flowable Electronics" by Marvin J. Slepian, filed on Oct. 8, 2014, the disclosures of which are incorporated by reference in their entirety.

FIELD OF THE INVENTION

The invention is generally directed to electronic devices that are flowable at the site of administration, and to methods of making and using such devices.

BACKGROUND OF THE INVENTION

Electronics and digital devices have become mainstream in modern life. From the calculator to the cell phone to the personal computer to the tablet all means of communication, data gathering and assembly, commerce and transmission of knowledge flow through these systems. In the health and medical arena increasingly electronic systems are utilized for diagnostic and therapeutic systems. Electronics are employed to sense, measure, analyze, store, and/or transmit data. Systems have become interactive and smart with either contained or remote actuation, allowing response, and correction or active therapy delivery. Electronics are employed in all disciplines of medicine, i.e. in cardiology—for rhythm detection; gastroeneterology—for viscus pacemakers; neurology—for deep brain stimulation; vascular medicine—for monitoring pulse and flow; and orthopedics—for bone regeneration. Devices are being deployed on the body or within the body. Electronic systems are becoming smaller and more durable.

Despite all these advances, a basic limitation exists to current electronic constructs. Electronics are fabricated from conductors and support materials. Conductive materials are generally stiff or rigid materials, such as metals, e.g. copper, platinum, tungsten or aluminum, or silicon, which is glassy and rigid. Similarly traditional support materials are typically rigid as well. However, biologic domains are generally flexible and compliant. Thus, there is a general "mismatch" between the material properties of the tissue or use domain to which the electronics are being applied and the material characteristics of the electronics themselves. While advances have been made recently in the development of flexible and stretchable electronics (see, e.g., U.S. Pat. No. 8,552,299 to Rogers, et al. and U.S. Published Application No. 2013/0041235 to Rogers, et al.) these constructs still remain large and bulky and with limited deformability.

Further an additional mismatch exists as to the site and nature of the location and topography of the biological sites to which electronics are needed. For example, often there is a need or desire to measure, monitor and/or treat an aspect or location of the body that is deep, isolated, protected or otherwise contained and walled off from direct access. Examples include, the Lung, e.g. measuring intra-pleural pressure in the pleural space; Heart, e.g. measuring intramyocardial pressure or local ventricular conduction; Surgical sites, e.g. measuring oxygen tension, pH, and/or temperature; Kidney, e.g. measuring pressure and/or flow of urine. To access any of these sites conventional approaches would use open surgery. However, these conventional approaches are highly invasive, add additional morbidity and the risk often outweighs any benefits gained from the intervention. As such the medical field in general has moved to less invasive and now minimally invasive approaches.

Minimally invasive and percutaneous technologies are used to access deep tissue structures, i.e. "privileged spaces," via hollow, low profile, small diameter access systems, with openings ranging in size from 30 gauge-12 gauge (needles) or 3 french to 21 french (1 french=0.3 mm) (catheters and sheaths) and even smaller.

There is a need for electronic devices and systems that are suitable for administration via minimally invasive and percutaneous technologies.

Therefore it is an object of the invention to provide electronic devices that can be delivered via minimally invasive and percutaneous technologies.

A further object of the invention is to provide electronic devices that can be poured, splashed, drizzled, misted or sprayed onto a surface.

It is a further object of the invention to provide methods for making and using such devices.

SUMMARY OF THE INVENTION

Electronic devices and systems that overcome the limitation of stiffness and rigidity generally associated with electronics and overcome the size limitations associated with minimally invasive and percutaneous access or delivery systems, such as narrow catheters, needles or trocars are described herein. Methods of making and using such devices and systems are also described.

The devices and systems are configured to be able to change in size, such as from a larger electronic construct going from a basal larger open, dispersed or "spread-out" size to a smaller "flowable" configuration, which allows for transport, movement or dispersal through a narrow tubular access means. The devices and systems are configured to open or reconfigure to return to the original size and spatial dimensions at the site. This allows the electronic device or system to be applied, adhere and conform to the underlying surface.

The device or system may be composed of either: (1) a contiguous mass, or (2) a discontinuous mass, i.e. made of components that may be smaller particles, packets, or contained substructure elements—which when re-apposed will have functional electronic continuity, electrical contact or transmissibility of signal so as to recapitulate to an original device, or (3) various combinations of (1) and (2).

In one embodiment, the devices and systems contain two or more electrical elements attached via interconnects, optionally on a supportive substrate. These devices and systems are configured to change from a non-fluent state to a fluent state, and then return to a non-fluent state, such as by opening or reconfiguring to return to the original size and spatial dimensions at a site in a patient. In another embodiment, the devices and systems begin as a plurality of discrete electrical elements in a flowable state, and change to a non-fluent state thereby forming the final electrical construct at a site in the patient. The electrical elements are able to communicate by direct contact with each other or by Bluetooth device or other near field inter-device communication means. Both of these embodiments, allow the electronic device or system to be applied, adhere and conform to the underlying surface.

While the flowable electronic devices and systems described herein can be delivered by passing through a narrow tube or conveyance, the applicability of this technology is not limited to this means of application, transport or delivery. Allowing electronics to have a fluent nature allows electronic devices or system, or components thereof (which when assembled at the site of use are "functional" via the nature of their ability to communicate, talk or otherwise interact with each other) to be applied to or within the body or any surface or location—animate or inanimate, via application means that take advantage of a fluent configuration.

The flowable electronics may be applied via brushing, rolling, spraying, dapping, spreading, smearing or "buttering" them on to a surface or site. Flowable electronics may be poured, splashed, drizzled, misted, or sprayed onto a surface or locale. In general flowable electronics utilize as an advantage the intrinsic rheological property of the ability of the device, system, or components thereof to flow and disperse.

BRIEF DESCRIPTION OF THE DRAWINGS

As shown in FIG. 4C, the discrete electronic components can communicate by direct contact with each other or by Bluetooth device or other near field inter-device communication means.

DETAILED DESCRIPTION OF THE INVENTION

I. Definitions

Figures 1A, 1B, 1C:
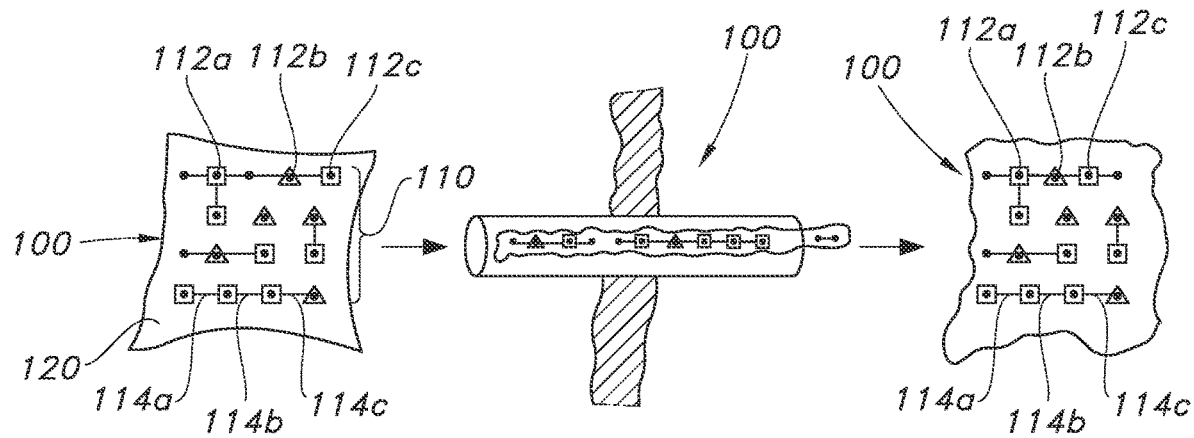
FIGS. 1A, 1B and 1C is three illustrations showing a device containing an electronic construct and a supportive substrate (also referred to herein as "support"), as it changes in configuration from a first expanded state (FIG. 1A), to a more compact flowable state (FIG. 1B), and finally back to a more expanded state that is similar to the first state (FIG. 1C).

The terms "actuating element" and "actuator", as used interchangeably herein, refer to a device component useful for interacting with, stimulating, controlling, or otherwise affecting an external structure, material or fluid, for example a biological tissue. Useful actuating elements include, but are not limited to, electrode elements, electromagnetic radiation emitting elements, sound and ultrasound elements, light emitting diodes, and lasers and heating elements. Exemplary actuating elements include electrodes for providing a voltage or current to a tissue, sources of electromagnetic radiation for providing electromagnetic radiation to a tissue, ablation sources for ablating tissue, ultrasonic elements for tissue stimulation or thrombus dispersion, thermal sources for heating tissue, and displacement sources for displacing or otherwise moving a tissue.

A "component", as used herein, broadly refers to a material or individual component used in a device or system. An electronic element is an example of a component of a device or system. An "interconnect" is one example of a component and refers to an electrically conducting material capable of establishing an electrical connection with a component or between components. An interconnect may establish electrical contact between components that are separate and/or can move regarding each other. Depending on the desired device specifications, operation, and application, an interconnect is made from a suitable material. For applications where a high conductivity is required, typical interconnect metals may be used, including but not limited to copper, silver, gold, aluminum, iron, magnesium, and the like, and alloys. Suitable conductive materials further include semiconductors, such as silicon and Gallium arsenide (GaAs) and other conducting materials, such as indium tin oxide. In certain embodiments, the interconnect is an organic semiconductor, preferably a polymeric organic semiconductor.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. A stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

The term "flexible" refers to the ability of a material, structure, device or device component to be deformed into a curved or bent shape without undergoing a transformation that introduces significant strain, such as strain characterizing the failure point of a material, structure, device or device component. In some embodiments, a flexible material, structure, device or device component may be deformed into a curved shape without introducing strain larger than or equal to 5%, for some embodiments larger than or equal to 1%, and for yet other embodiments larger than or equal to 0.5% in strain-sensitive regions. A used herein, some, but not necessarily all, flexible structures are also stretchable. A variety of properties provide flexible structures (e.g., device components), including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries. In this description, a "bent configuration" refers to a structure having a curved conformation resulting from applying a force. Bent structures may have one or more folded regions, convex regions, concave regions, and any combinations thereof. Useful bent structures, for example, may be in a coiled conformation, a wrinkled conformation, a buckled conformation and/or a wavy (i.e., wave-shaped) configuration. Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than 30%, optionally a strain equal to or less than 10%, optionally a strain equal to or less than 5% and optionally a strain equal to or less than 1% in embodiments preferred for some applications. In some embodiments, the bent structure, such as a bent ribbon structure, is under a strain within the range of 0.5% to 30%, optionally a strain within the range of 0.5% to 10%, and optionally a strain within the range of 0.5% to 5%. Alternatively, the stretchable bent interconnects may be bonded to a substrate that is a substrate of a device component, including a substrate that is itself not flexible, The substrate itself may be planar, substantially planar, curved, have sharp edges, or any combination thereof. Stretchable bent interconnects are available for transferring to any one or more of these complex substrate surface shapes.

As used herein, the term "microparticle" generally refers to a particle having a diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape may be referred to as "microspheres."

As used herein, the term "nanoparticle" generally refers to a particle having a diameter, from about 1 nanometer to 1000 nanometers, preferably from about 10 nanometers to 1000 nanometers, more preferably from about 100 nanometers to 1000 nanometers, most preferably from about 250 nanometers to 1000 nanometers. The nanoparticles can have any shape. Nanoparticles having a spherical shape may be referred to as "nanospheres."

II. Devices, Systems and Methods for Imparting Flowability

Electronic devices that are designed to be flowable at the site of administration, and methods for making and using such devices are disclosed herein. The devices may be administered to human patients, or other animals, at a variety of sites in the body, such as, within the patient's circulatory and/or digestive systems. The devices may be transient biodegradable devices or made from non-biodegradable materials. The devices may be expandable and contractable. For example, the devices may be in the form of a flat planar material that is compressible into a micro- or nano-sized particle.

The devices may communicate or interact with other electronic devices, optionally flowable electronic devices, to form a network relaying information between flowable devices and/or relaying information with non-flowable devices that are located internally or externally. The devices may operate as or within a set of nested loops.

A. Devices

The devices and systems include one or more electronic components, optionally connected via interconnects. Optionally, the device contains a supportive substrate.

Optionally, the entire device is biodegradable or bioerodible.

1. Electronic Components

The devices include one or more electronic components. Examples of electronic components, but are not limited to sensors, data storage and processing means, telemetry means, actuators—e.g. nerve stimulation, pacemaking, drug delivery means, power generation (i.e. piezoelectric materials), power and/or data receiving/transmitting means, and/or data storage means.

The electronic components are capable of communicating with each other to store, transmit and/or receive data. Optionally, the electronic components are able to locally monitor, enhance, attenuate, and/or impact the function of an organ or organ component.

a. Materials

Electronic components can be made from magnesium, iron, silver, copper, tin, lead, actinide metals, lanthanide metals, alkali metals, alkaline-earth metals, noble metals, rare metals, rare-earth metals, or transition metals or alloys thereof. Electronic components can be made from a variety of materials and alloys such as those described in Ricker et al. (1994), "Corrosion of Metals" pgs. 669-728 in "Evaluation of Alternative In-Flight Fire Suppressants for Full-Scale Testing in Simulated Aircraft Engine Nacelles and Dry Bays. Section" edited by Grosshandler et al. NIST, 1994. The materials forming the electronic components can be chosen based upon available rates of degradation or corrosion to choose the desired rate of degradation of the electronic device or component.

The electronic component may include a semiconducting material that is biodegradable, such as thin or ultra-thin silicon.

The flowable devices can be any type of electronic component, including but not limited to capacitors, inductors, resistors, diodes, transistors, interconnects, and crossovers.

In some embodiments, the electronic components are biodegradable or bioerodible.

The one or more electronic components may be connected via one or more interconnects. An "interconnect" refers to an electrically conducting material capable of establishing an electrical connection with a component or between components. An interconnect may establish electrical contact between components that are separate and/or can move regarding each other. Suitable materials for an interconnect depend on the particular device specifications, operation, and application. For applications where a high conductivity is required, typical interconnect metals may be used, including but not limited to copper, silver, gold, aluminum and the like, and alloys. Suitable conductive materials further include semiconductors, such as silicon and Gallium arsenide (GaAs) and other conducting materials, such as indium tin oxide. In certain embodiments, the interconnect is an organic semiconductor, preferably a polymeric organic semiconductor.

2. Supportive Substrate

In some embodiments, one or more electronic components are attached to or integrated into a polymeric material or scaffold, which serves as a supportive substrate (or "support") for the electronic components.

In some embodiments, the polymeric scaffold serves as a controlled release matrix or contains a controlled release polymer matrix, capsule or reservoir means for delivery of one or more therapeutic or diagnostic agents.

a. Change in Size

The support is flexible and can change in size. The support can be large but typically must elongate to fit through the desired internal dimension of the application means. As shown in FIGS. 1A and 1B, the support may be sufficiently flexible to allow it to roll up into a suitable form for fitting through a trocar, catheter or needle.

The support is configured to be converted to a fluent state. This can occur via numerous means including but not limited to heating and softening, hydrating—swelling and/or partially solvating or dissolving, changing phase, electrically activating or the like.

b. Micro or Nanoparticles or Capsules

In other embodiments, the support is a micron-sized or nanometer-sized particle. For example, the particles can range in size from about 100 nanometers (the virus-like particles, e.g. made by nanotechnologic/chip technology means) to the larger particles, such as macro particles or packets having sizes ranging from 3 to 4 mm. Typical particle or capsule sizes range from 500 nm-2 mm.

One or more electronic elements, optionally with interconnects, can be attached to or encapsulated by the micro- or nano-particles. The one or more electronic elements may be coated on, dispersed in, embedded in, encapsulated in the micro- or nano-capsules or particles.

The particles can be biodegradable or nonbiodegradable.

3. Carrier

One or more electronic devices can be administered to a patient in combination with a suitable carrier. The carrier is typically a flowable material, such as an inert, biocompatible liquid.

The fluent material (carrier with one or more electronic devices) may have any suitable form, as long as it is fluent, such as a dispersion, a sol, a gel, a solution, or other fluent means. This fluent material (including the electronic elements) is then applied to a surface using a suitable application device or system, such as to spray, brush, or roll the material onto the surface.

In some embodiments, the devices are in the form of a plurality of particles, which are dispersed or suspended in a pharmaceutically acceptable carrier. Generally the plurality of particles is dispersed or suspended in the carrier immediately before it is administered. Suitable carriers include, but are not limited to an appropriate buffer, for example, phosphate buffered saline and other physiologically compatible solutions. Surfactants such as polysorbates (TWEEN™, e.g. polysorbate 20 or polysorbate 80), or polyethylene glycol, sodium lauryl sulfate, sodium caprate, pluronics (triblock copolymer of PEO-PPO-PEO), Sorbitane monooleate (Span® 80, Sigma Aldrich), or lecithin, or a combination thereof may be incorporated into the suspension or dispersion as needed.

Optionally, the carrier is a fluent material that is able to solidify following delivery to the desired site. Solidification can occur by any suitable means, including but not limited to by application of light, temperature change, by an electrical current, ultrasound, polymerization, or interaction with biological fluid.

III. Exemplary Devices and Systems and Methods for Creating Flowable State

A. Device Containing Electronic Constructs with Flexible Interconnects or Traces and Method for Creating Flowable State In one embodiment, the device contains a plurality of small electronic components and a plurality of interconnects that are flexible and elongatable and/or stretchable that form an electronic construct. The electronic construct may be on or in a supportive substrate (see, FIGS. 1A, 1B, and 1C).

An electronic device in its expanded state is shown in FIG. 1A. The device 100 is composed of an electronic construct 110 and a supportive substrate 120. The electronic construct 110 is composed of individual discrete electronic elements 112a, b, c (collectively 112), several of which may be interlinked or interconnected via flexible interconnects or traces (114a, b, and c; collectively 114). The interconnects or traces are flexible and elongatable.

The construct 110 is mounted on or contained within the supportive substrate 120. The supportive substrate is configured to be converted to a fluent state. This can occur via numerous means including but not limited to heating and softening, hydrating—swelling and/or partially solvating or dissolving, changing phase, electrically activating or the like.

As the substrate becomes flowable, coupled with the flexibility and elongatability of interconnects or traces, the entire device becomes flowable and fluent. This allows passage of the flowable device through an application trocar or catheter as shown in FIG. 1B. Other devices for applying or delivering the flowable device to a site in a patient's body or to the surface of an inanimate object may be used in place of the trocar or catheter illustrated in FIG. 1B.

As shown in FIG. 1C, once inside a patient's body at the desired site of application the device may be applied, unfurled or otherwise reconfigured to approximate its original configuration, such that the discrete electronic elements 112 are aligned and connected via interconnects 114 in the same configuration as initially present prior to delivery to the site, as depicted in FIG. 1A.

Figure 2A:
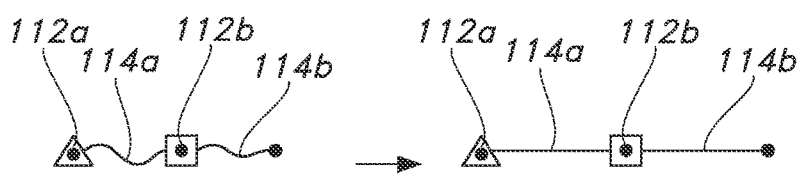
FIGS. 2A and 2B illustrate two examples of a device that contains electronic components attached via flexible interconnects, in the absence of a supportive substrate. The left side of FIGS. 2A and 2B shows the devices in their compressed state, while the right side shows the devices in their elongated state. In the elongated state, these devices are essentially linear and can be flowable and delivered via a device with a narrow tubular access means.
Figure 2B:
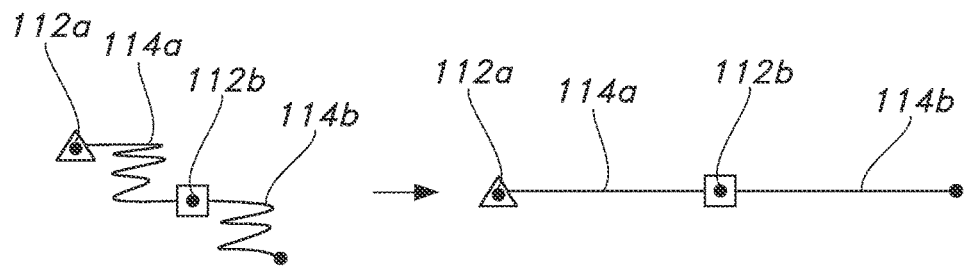

Alternatively, as shown in FIGS. 2A and 2B, the electronic construct may not be in or on a supportive substrate. FIGS. 2A and 2B show two examples, of an electronic device that contains elongatable or redundant interconnects or traces 114a, b (collectively 114) between two or more electronic elements 112a, 112b (collectively 112). The flexible interconnects allow the device to change its overall length, width and/or depth dimensions from a more compressed state, which is shorter and wider, to an elongated state, i.e. linear, or nearly linear, dimensions. In the elongated, linear state, the device is able to pass through a relatively narrow application or delivery device.

B. System and Method for Forming Electronic Device In Situ Using Flowable Components The electronic device may be formed in situ by combining flowable components of the device, allowing them to contact each other in situ, and then delivering the resulting device to the desired site.

Figure 3:
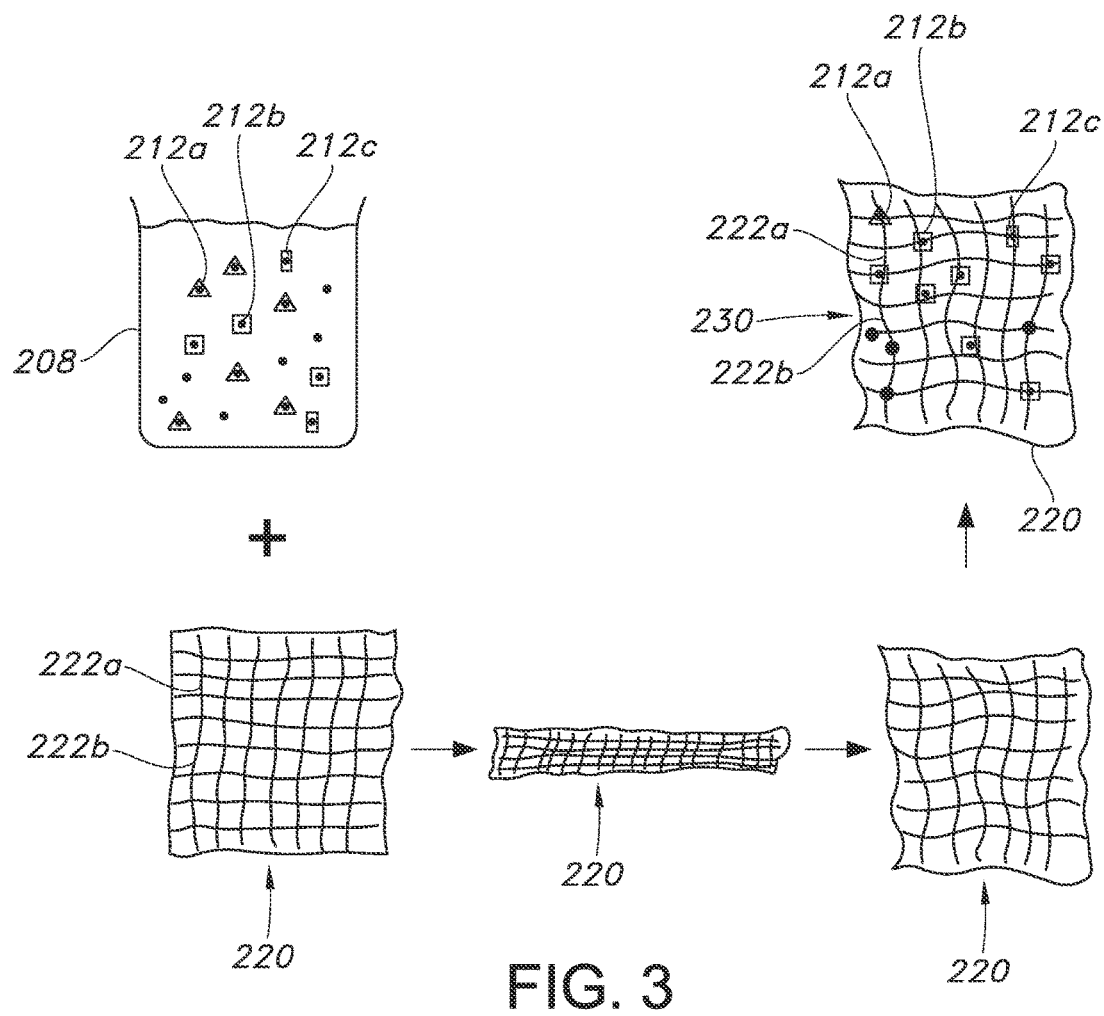
FIG. 3 illustrates a method of combining flowable components, such as discrete electronic components and a flexible and flowable interconnect material, to produce an electronic device in situ.

FIG. 3 depicts an exemplary system and method for applying flowable electronics 212a, b, c (collectively 212) utilizing a flowable backbone system (220) with contained interconnects or traces (222a, b collectively 222) to a desired site. As shown in FIG. 3, a plurality of small, discrete electronic elements 212 in a container 208 are applied to a flexible and flowable interconnect construct 222 to form a flexible, flowable electronic device 230. When this system is reconfigured in situ, the electronic elements then gain their "interconnectivity" by virtue of making contact or being proximate to the interconnects 222 and form the resulting electronic device 230.

C. System and Method for Discrete Electronic Elements to Communicate with Each Other in the Absence of Interconnects In another embodiment, the system contains a plurality of discrete electronic elements that are small and communicable, such that when in place they can act as a continuum whole that functions as a full device.

Figures 4A, 4B:
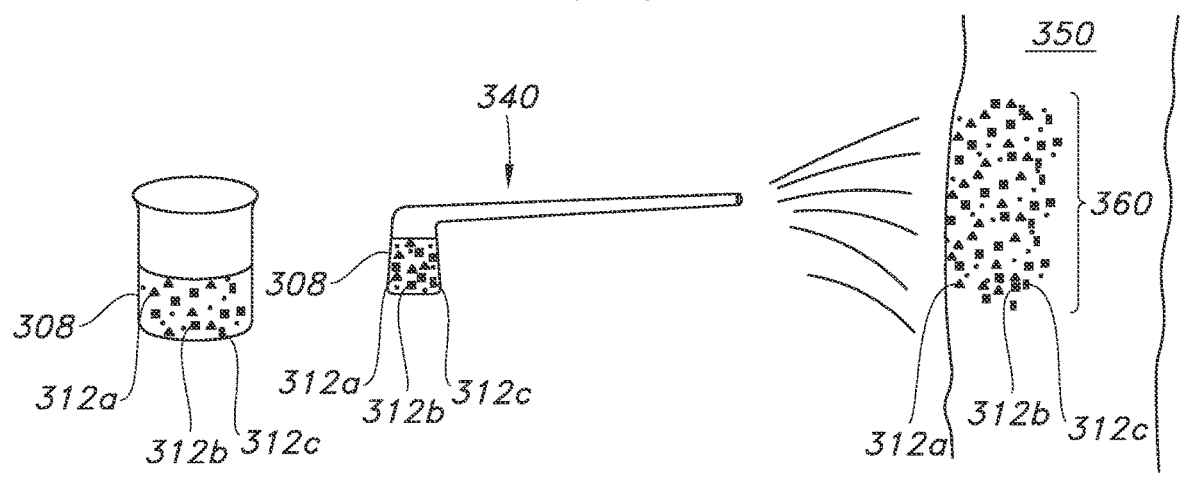
FIGS. 4A, 4B and 4C depict systems with a plurality of electronic components in a fluent medium (FIG. 4A), which can be applied to a desired surface, such as by spraying (FIG. 4B).

As shown in FIGS. 4A and 4B a mass of flowable electronic elements 312a, b, c (collectively 312) in a fluent medium contained in the container 308 may be placed in or attached to an application system or device 340 and dispersed on a surface 350. In this example, the electronic elements 312 are shown as sprayed on to the surface 350.

The sprayed material forms a coating 360 containing a plurality of electronic elements 312, where the elements can communicate with each other via direct contact or via a contained means to allow electrical interaction, such as for example via Bluetooth or near field communication.

Figure 4C:
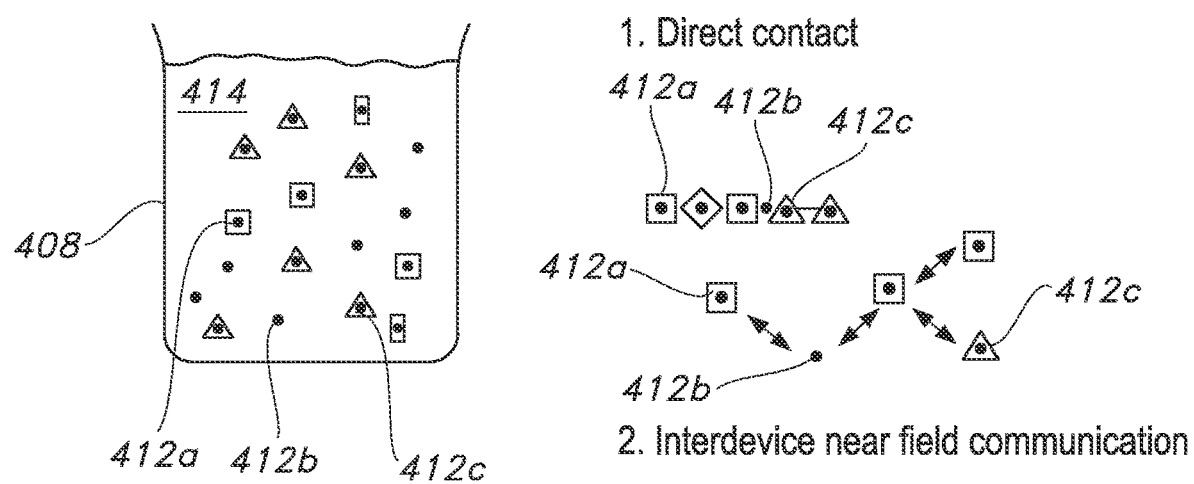

As shown in FIG. 4C, a plurality of discrete electronic elements (412*a, b, c*; collectively 412) may be dispersed in a flowable medium 414 contained in a container 408. The material in the container can be applied to a surface via a suitable application device to apply the electronic elements onto the surface. The elements can then communicate via direct contact or via contained means to allow electrical interaction, e.g. via Bluetooth or near field communication.

1. Fluent Medium or Carrier

The fluent medium (also referred to hearing as a carrier) may be any flowable material. It may be aqueous or non-aqueous. Typically the fluent medium has an adequate viscosity to suspend or disperse the elements, such as for example ranging from 0-20,000 centistokes, with consistencies like glycerol, honey and/or motor oil.

A plurality of electronic elements (optionally in or on one or more support elements, such as one or more nano- or micro-particles) may be provided in a fluent medium. The resulting fluent material (carrier with one or more electronic devices) may have any suitable form, as long as it is fluent, such as a dispersion, a sol, a gel, a solution, or other fluent means. This fluent material (including the electronic elements) is then applied to a surface using a suitable application device or system, such as a sprayer, brush, roller, or other application device.

IV. Uses

The devices described herein can be used in all disciplines of medicine, Examples include but are not limited to cardiology, e.g. for rhythm detection; gastroenterology, e.g. for viscous pacemakers; neurology, e.g. for deep brain stimulation; vascular medicine, e.g. for monitoring pulse and flow; and orthopedics, e.g. for bone regeneration. The devices described herein may be used in the lung, such as for measuring intra-pleural pressure in the pleural space. In another embodiment, the devices may be used in the heart, such as for measuring intramyocardial pressure or local ventricular conduction. The devices by be applied to a surgical site, such as for measuring oxygen tension, pH, and/or temperature at the site. Alternatively, the devices may be used in the kidney, such as to measure pressure or flow of urine.

a. Medical Uses

One or more devices, preferably a plurality of devices can be mixed with a liquid carrier and administered by spraying, brushing, rolling, or other application means or as a flowable liquid.

The devices may be administered to a site in a patient via needles, trochars, sheaths or catheters,—i.e. hollow, low profile, small diameter access systems. Typically these devices range in diameter from 30 gauge-12 gauge (needles) or 3 french to 21 french (where 1 french=0.3 mm) (catheters and sheaths). However, the application devices may be even smaller.

b. Non-Medical Uses

In some embodiments, the flowable electronic devices are used in non-medical applications. In these embodiments, the devices may be applied to the desired surface in the form of or included in paints, sprays, and/or coatings.

I claim:

1. A flowable electronic device or system for administration to a site in an animal comprising electronic elements and a biocompatible carrier, wherein the carrier is a fluent material, wherein the electronic elements are attached to each other via flexible interconnects or wherein each of the electronic elements is discrete and is configured to electronically communicate with the other electronic elements, wherein the device or system is configured to be administered to the animal in a fluent state, and wherein the device or system converts from the fluent state to a non-fluent state on a surface of the site in the animal in situ and conforms to the surface of the site in the animal.

2. The device or system of claim 1, wherein the electronic elements are attached to each other via flexible interconnects.

3. The device or system of claim 1, further comprising a supportive substrate configured to change from a non-fluent state to a fluent state.

4. The device or system of claim 3, wherein the supportive substrate comprises one or more flexible interconnects, wherein the interconnects are attached to the electronic elements.

5. The device or system of claim 4, wherein the supportive substrate further comprises the electronic elements.

6. The device or system of claim 3, wherein the supportive substrate is in the form of one or more micro- or nano-particles or capsules.

7. The device or system of claim 1, wherein the device or system does not contain a supportive substrate.

8. The device or system of claim 1, further comprising near field communication, Bluetooth, or telemetry of other communication means, and wherein each of the electronic elements is discrete and is configured to electronically communicate with the other electronic elements via the near field communication, Bluetooth, or telemetry of other communication means.

9. A method of delivering electronics to a surface of a site in an animal comprising delivering one or more devices or systems defined by claim 1 to the animal by spraying, brushing, pouring, splashing, drizzling, or misting or through a narrow tube.

10. The method of claim 9, wherein the narrow tube is a catheter, a trocar, or a needle.

11. The method of claim 9, further comprising converting the device or system from a fluent state to a less fluent state.

12. The method of claim 9, comprising delivering the one or more devices or systems to the patient by spraying, brushing, pouring, splashing, drizzling, or misting.

13. The method of claim 9, wherein the site in the patient is not directly accessible.

14. The method of claim 13, wherein the site is located on or in the lung, the heart, or the kidney.

15. The method of claim 9, wherein the electrical elements measure, monitor and/or treat an aspect or location of the site.

16. The method of claim 9, wherein the device or system adheres and conforms to the surface of the site.

17. The device or system of claim 1, wherein the biocompatible carrier is a dispersion, a sol, a gel, or a solution.

18. The device or system of claim 1, wherein the animal is a human.

19. The device or system of claim 1, wherein the electronic elements are biodegradable or bioerodible.

20. The device or system of claim 1, wherein the device or system is in a form suitable for delivery to the surface of the site in the animal by spraying, brushing, pouring, splashing, drizzling, or misting, or through a narrow tube.

\* \* \* \* \*